US011478127B2

(12) United States Patent
Ailinger et al.

(10) Patent No.: US 11,478,127 B2
(45) Date of Patent: Oct. 25, 2022

(54) THIN-WALLED SPIRAL TUBE FOR USE WITH ENDOSCOPE

(71) Applicant: OLYMPUS CORPORATION, Tokyo (JP)

(72) Inventors: Robert E. Ailinger, Norwood, MA (US); David Gately, Maynard, MA (US); Matthew S. Carlone, Marlborough, MA (US)

(73) Assignee: OLYMPUS CORPORATION, Tokyo (JP)

( * ) Notice: Subject to any disclaimer, the term of this patent is extended or adjusted under 35 U.S.C. 154(b) by 805 days.

(21) Appl. No.: 16/367,522

(22) Filed: Mar. 28, 2019

(65) Prior Publication Data

US 2020/0305689 A1    Oct. 1, 2020

(51) Int. Cl.
*F16L 11/11* (2006.01)
*A61B 1/00* (2006.01)
*A61B 1/005* (2006.01)
*A61M 25/00* (2006.01)
*B29C 45/26* (2006.01)
*A61B 17/00* (2006.01)

(52) U.S. Cl.
CPC .......... *A61B 1/00071* (2013.01); *A61B 1/005* (2013.01); *A61B 1/0011* (2013.01); *A61B 1/00147* (2013.01); *A61M 25/0012* (2013.01); *A61M 25/0021* (2013.01); *B29C 45/2612* (2013.01); *A61B 1/00131* (2013.01); *A61B 2017/00526* (2013.01); *F16L 11/11* (2013.01); *F16L 11/111* (2013.01)

(58) Field of Classification Search
CPC ................................. F16L 11/11; F16L 11/111
USPC .................................. 138/121, 122, DIG. 11
See application file for complete search history.

(56) References Cited

U.S. PATENT DOCUMENTS

| 4,151,864 A | * | 5/1979 | Thurman | ................ F16L 3/003 138/121 |
| 4,274,549 A | * | 6/1981 | Germain | .............. B60K 15/035 285/123.17 |
| 4,756,045 A | * | 7/1988 | Gans | ........................ A47L 9/24 181/207 |

(Continued)

FOREIGN PATENT DOCUMENTS

JP    5985132 B1    9/2016

OTHER PUBLICATIONS

International Search Report dated Jun. 17, 2020 together with the Written Opinion received in related International Application No. PCT/JP2020/013852.

(Continued)

*Primary Examiner* — Patrick F Brinson
(74) *Attorney, Agent, or Firm* — Scully, Scott, Murphy & Presser, P.C.

(57) ABSTRACT

A polymeric device including: an elongated hollow tube having an outer surface; and a spiral fin wound around the outer surface of the hollow tube; wherein the hollow tube and the spiral fin are formed of a single unitary piece through a molding process. The polymeric device can further include a longitudinal projection projecting from the outer surface of the hollow tube, the longitudinal projection having a greater thickness than other portions of the hollow tube and the longitudinal projection extending at least a portion of a longitudinal length of the hollow tube.

13 Claims, 9 Drawing Sheets

(56) References Cited

U.S. PATENT DOCUMENTS

| | | | | |
|---|---|---|---|---|
| 5,925,855 | A * | 7/1999 | Denndorfer | H01B 17/325 |
| | | | | 174/212 |
| 5,938,587 | A * | 8/1999 | Taylor | A61B 1/018 |
| | | | | 600/123 |
| 6,116,289 | A * | 9/2000 | Hayashi | F16L 25/0036 |
| | | | | 138/121 |
| 6,394,145 | B1 * | 5/2002 | Bailly | F16L 11/24 |
| | | | | 156/428 |
| 6,464,632 | B1 * | 10/2002 | Taylor | A61B 1/005 |
| | | | | 138/174 |
| 6,969,397 | B2 * | 11/2005 | Ginn | A61B 17/0057 |
| | | | | 600/585 |
| 7,891,382 | B2 * | 2/2011 | Rushlander | F16L 11/112 |
| | | | | 138/119 |
| 8,936,047 | B2 * | 1/2015 | Hahn | B29C 48/09 |
| | | | | 138/121 |
| 2006/0213567 | A1 * | 9/2006 | Parpart | F16L 11/11 |
| | | | | 138/121 |
| 2010/0069718 | A1 | 3/2010 | Frassica et al. | |
| 2013/0284302 | A1 * | 10/2013 | Castro | F16L 11/16 |
| | | | | 138/109 |
| 2014/0206942 | A1 | 7/2014 | Webb | |

OTHER PUBLICATIONS

European Office Action dated Sep. 1, 2022 received in 20 719 771.6.

* cited by examiner

THIN-WALLED SPIRAL TUBE FOR USE WITH ENDOSCOPE

BACKGROUND

1. Field

The present disclosure relates generally to thin-walled tubes and more particularly to thin-walled spiral tubes for use with an endoscope and/or endoscope system.

2. Prior Art

In general, an insertion section of an insertion apparatus, such as an endoscope, is inserted into, for example, a lumen. One type of such an endoscope inserted into a lumen which is known is a self-propelled insertion apparatus.

In such a rotary self-propelled insertion apparatus, a rotating cylindrical body called a spiral tube is provided, on which a spiral fin is formed on a thin-walled tube. The spiral tube is rotatably disposed on an outer circumferential face of an insertion section of the endoscope. When the spiral tube rotates, the spiral fin contacts an inner wall of the lumen, thus generating a propulsion force. By this propulsion force, the insertion section is propelled in a direction of insertion or in a direction of removal.

If the thin-walled tube and spiral fin are formed of a single unitary part, the spiral tube presents a very challenging molded part to fill completely during an injection molding process. This is due to the thin-walled tube portion of the spiral tube producing a high resistance to the molten material flow due to its very thin wall, which typically can be about 0.018 inches thick. The definition of "thinwall" is dependent on many factors which contribute to the problem of resin not flowing to ends of an injection molded tube, such as the material flow characteristics, resin pressure, gating, part geometry, and flow length, to name a few. Injection molding of thin-walled tubes generally result in an end of the thin-walled tube being incompletely formed because the molten material being injected into the mold cavity has too much resistance to flow due to the thin wall and does not flow completely to the ends of the thin-walled tube.

Because of such problems, conventional spiral tubes are formed of a thin wall tube with a spiral fin attached to the outer circumference of the tube as a secondary operation, such as by the application of Ultraviolet (UV) cure acrylic adhesives, which requires precision dispensing and locating and by calibrated light curing. Such spiral tubes include many additional steps for formation along with an associated increase in manufacturing and quality control costs.

SUMMARY

Accordingly, a polymeric device is provided. The polymeric device comprising: an elongated hollow tube having an outer surface; and a spiral fin wound around the outer surface of the hollow tube; wherein the hollow tube and the spiral fin are formed of a single unitary piece through a molding process.

The polymeric device can further comprise a longitudinal projection projecting from the outer surface of the hollow tube, the longitudinal projection having a greater thickness than other portions of the hollow tube and the longitudinal projection extending at least a portion of a longitudinal length of the hollow tube.

The longitudinal length of the longitudinal projection can extend from a portion of the spiral fin nearest an end of the hollow tube to the end of the hollow tube.

The polymeric device can further comprise an end ring formed at an end of the hollow tube, the end ring having a thickness projecting from the outer surface of the hollow tube, the longitudinal length of the longitudinal projection extends from a portion of the spiral fin nearest the end of the hollow tube to the end ring.

The longitudinal projection can extend at least the portion of the longitudinal length of the hollow tube at a single circumferential position.

Also provided is a polymeric tubular member comprising: an elongated hollow tube having an outer surface; a spiral fin wound around the outer surface of the hollow tube; and a longitudinal projection projecting from the outer surface of the hollow tube, the longitudinal projection having a greater thickness than other portions of the hollow tube and the longitudinal projection extending at least a portion of a longitudinal length of the hollow tube; wherein the hollow tube, the spiral fin and the longitudinal projection are formed of a single unitary piece through a molding process.

The longitudinal length of the longitudinal projection can extend from a portion of the spiral fin nearest an end of the hollow tube to the end of the hollow tube.

The polymeric tubular member can further comprise an end ring formed at an end of the hollow tube, the end ring having a thickness projecting from the outer surface of the hollow tube, the longitudinal length of the longitudinal projection extends from a portion of the spiral fin nearest the end of the hollow tube to the end ring.

The longitudinal projection can extend at least the portion of the longitudinal length of the hollow tube at a single circumferential position.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

While the disclosed embodiments have particular utility for use with thin-walled spiral tubes for use with endoscopes and are described below with regard to the same, the apparatus and methods disclosed herein are not so limited and have utility to other types of thin-walled tubes, with or without projections extending therefrom.

Figure 1:
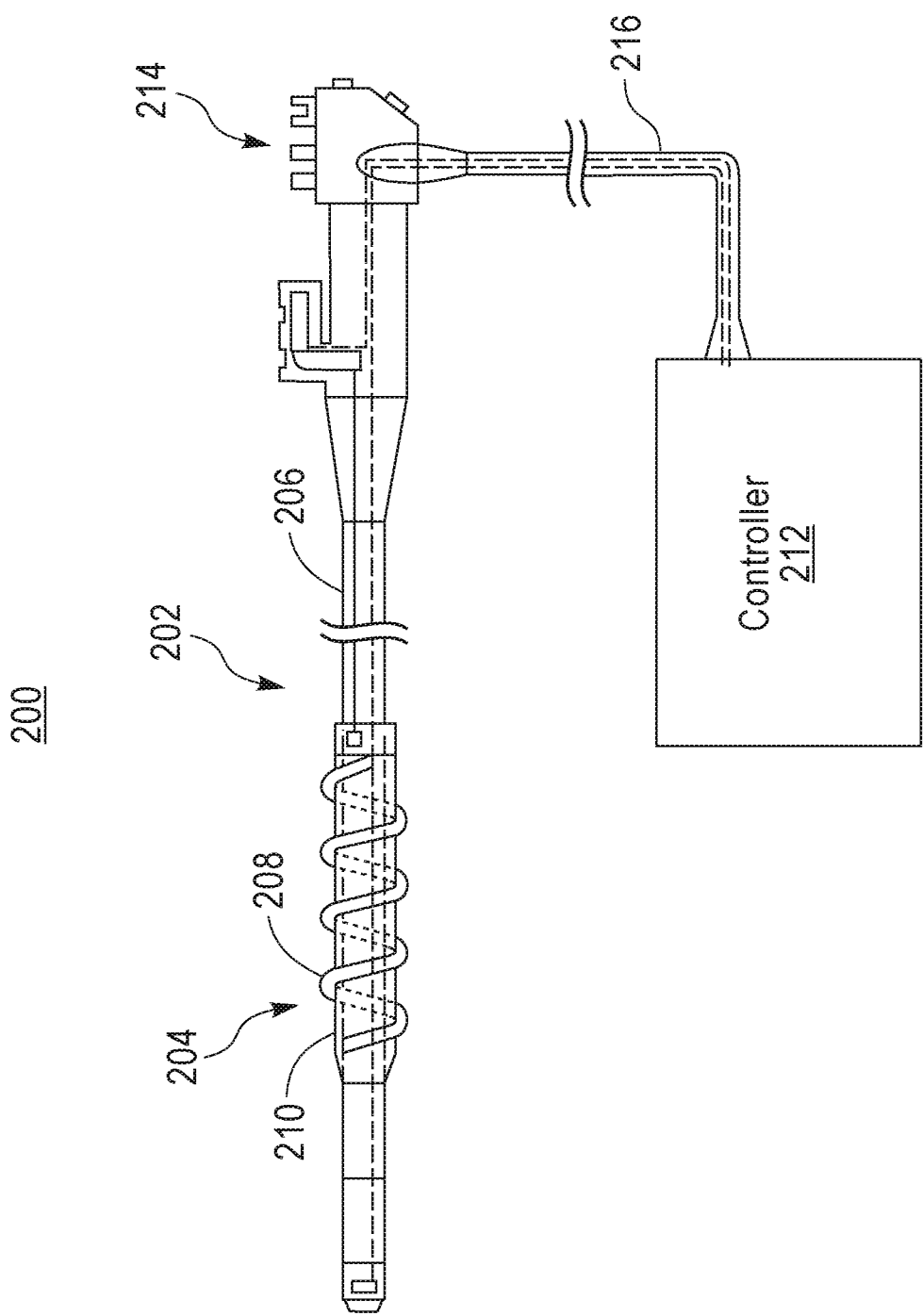
FIG. 1 illustrates an endoscope system having a spiral tube rotatably disposed on an insertion section of an endoscope.

Referring now to FIG. 1, the same illustrates an endoscope system 200 having a spiral tube 204 rotatably disposed on an insertion section 206 of an endoscope 202. The spiral tube 204 is formed in a cylindrical form using an elastic material such as rubber, resin, etc. (generally referred to as a "polymeric tube"), and is rotatably attached to the insertion section 206 around its longitudinal axis. The spiral tube 204 includes a spiral-shaped fin 208 provided on an outer circumferential face of a spiral tube 210 such that the spiral-shaped fin 208 extends along a longitudinal length of the spiral tube 210. The spiral tube 204 can be configured to be detachable from the insertion section 206.

The spiral tube 204 is connected to a motor provided as an actuator. The motor is connected to a controller 212 via a signal line for motor current signals that pass through an endoscope control body 214 and a universal cable 216 connecting the endoscope 202 and controller 212.

When the spiral tube 204 rotates in contact with a wall, such as an inner wall of a lumen, a propulsion force that propels the insertion section 206 is generated. In the small intestine or the large intestine, for example, the spiral fin 208, rotating along with the spiral tube 204, crawls along the folds on the inner wall of the small intestine or the large intestine, and thereby a propulsion force acts on the insertion section 206. By this propulsion force, the insertion section 206 is propelled. The self-propulsion of the insertion section 206 assists in the tasks of insertion and removal of the insertion section 206 by the user.

Figure 2:
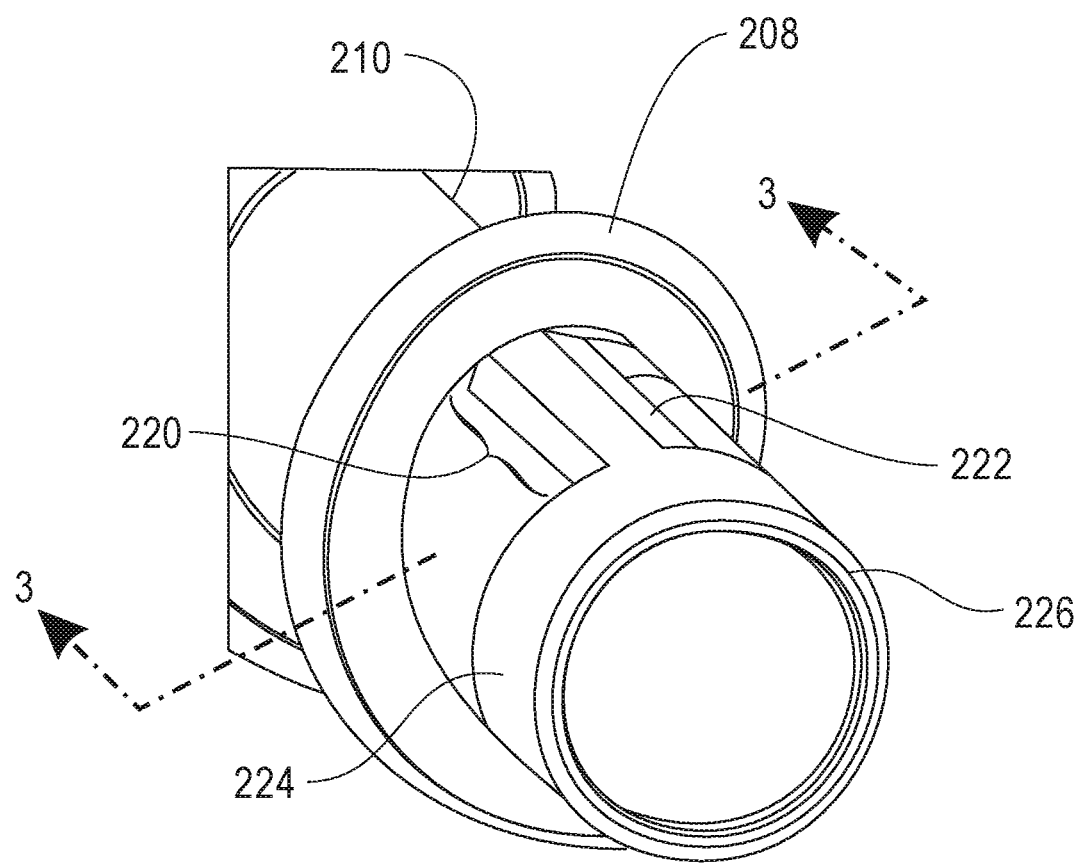
FIG. 2 illustrates an end of the spiral tube of FIG. 2 having an internal flow channel and associated end ring.

Turning next to FIG. 2, the same illustrates an end of the spiral tube 204 having the thin-walled tube 210 and the spiral fin 208 integrally formed as a single unitary piece by injection molding. Another end of the spiral tube 204 can have the same configuration as that of the end illustrated in FIG. 2, therefore, such other end is not described or illustrated in FIG. 2 for the sake of brevity. The injection molding process includes a series of runners and gates which provide the molten material to a cavity having the form of the spiral tube 204. Such gates typically provide a flow of the molten material to several places at an outermost circumferential position or face of the spiral fin 208. In turn, the spiral fin 208 typically acts as a gate to provide the molten material to the thin-walled tube 210 portion of the spiral tube 204. However, in conventional spiral tubes, as discussed above with regard to FIG. 1, some portions of the thin-walled tube may not fully fill with the injected molten material, particularly, at the ends of the thin-walled tube where no, or very little, portions of the spiral fin are present, or at portions of the thin-walled tube between spiral fin projections.

Figure 3:
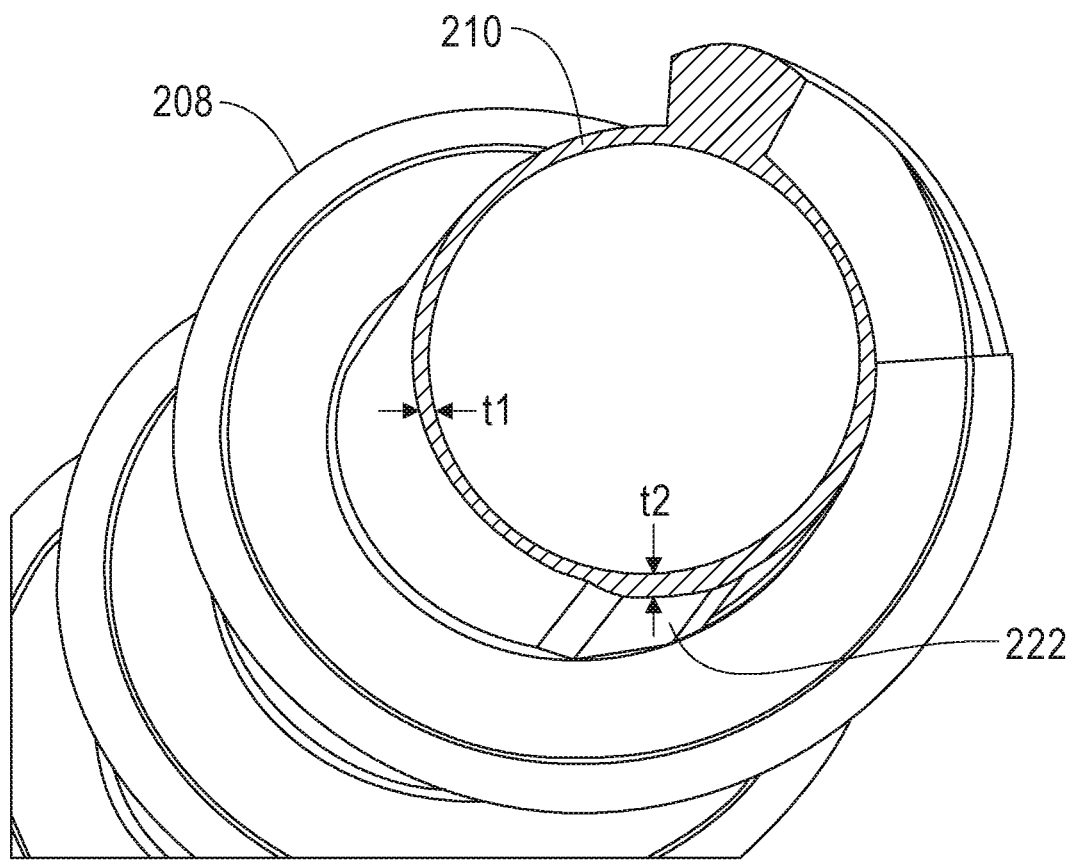
FIG. 3 illustrates a sectional view of the spiral tube of FIG. 3 as taken along line 3-3 in FIG. 2.

Referring now to FIGS. 2 and 3, an end portion 220 of the spiral tube 204 includes an internal flow channel 222 in the form of a longitudinal projection having an increased thickness in a radial direction of the thin-walled tube 210. Such internal flow channel 222 is integrally formed with the thin-walled tube 210 and has a thickness and circumferential width sufficient to increase the flow of the injected molten material such that the molten material fully and completely fills the end of the thin-walled tube 210. The thickness and width of the internal flow channel 222 can vary depending on several factors including the material flow characteristics, gating, part geometry, flow length and injection pressure. The thickness and or width of the internal flow channel 222 is/are a compromise between allowing the resin to flow to the end of the thin-walled tube 210 during injection molding and avoiding detrimentally increasing stiffness of the thin-walled tube 210. Sides of the internal flow channel 222 can be angled or curved to form a smooth transition from the outer circumferential surface of the thin-walled tube 210 to an upper surface of the internal flow channel 222. Although illustrated as having a constant thickness along its longitudinal length, the internal flow channel 222 may alternatively have a varying thickness along its length, such as tapering from a greater thickness nearer the spiral fin 208 as compared to a thickness nearer an end of the thin-walled tube 210.

When the internal flow channel 222 is provided at the end(s) 220 of the spiral tube 204, the longitudinal length of the internal flow channel 222 can be from a nearest spiral fin portion to a further point on an end 226 of the thin-walled tube 210 so as to provide the flow of the molten material from the nearest fin to the end 226. Since the spiral fin 208 may not be provided at the very end 226 of the thin-walled tube 210 or may taper off to a smaller diameter at the very end 226 of the thin-walled tube 210, the internal flow channel 222 can be formed at the circumferential position of the thin-walled tube 210 where no fin or the least portion of fin is provided so as to act as a gate for transferring the molten material to the end 226 of the thin-walled tube 210. Furthermore, the internal flow channel 222 can project radially outward from an external outer circumferential surface of the thin-walled tube 210. The internal flow channel can be alternatively disposed on the inner diameter of the thin-walled tube 210, for example if the surface is blended to conform with the rest of the thin-walled tube structure.

As discussed above, the internal flow channel 222 can terminate at the very end 226 of the thin-wall tube, or alternatively, as shown in FIG. 2, the internal flow channel 222 can terminate at an end ring 224 having an increased thickness, which can be a same thickness as the internal flow channel 222. The end ring 224 being in communication with the internal flow channel 222 when molten material is injected in a corresponding mold cavity for the spiral tube 204.

Although the internal flow channel 222 is illustrated with regard to being positioned at the end(s) 226 of the thin-walled tube 210, an internal flow channel can terminate just prior to the end or it can be positioned anywhere along a longitudinal length of the thin-wall tube 210, such as between one or more of the turns of the spiral fin 208. Furthermore, although the internal flow channel 222 is described and illustrated as being provided in a single circumferential position, more than one internal flow channel 222 can be provided in the circumferential direction to provide symmetry in the circumferential direction, such as 60, 90, 120 or 180 degrees apart.

Although the internal flow channel 222 is described as a "flow channel," the same is only a flow channel while the spiral tube 204 is being molded. Thus, the term "flow channel" as discussed herein is also used to describe the thickened longitudinal projecting portion of the thin-walled tube that acts as a flow channel during the molding process to transfer molten injected material to flow through the same so as to completely fill a particular area, such as an end of the thin-walled tube, with molten material during the injection molding process.

Furthermore, although the spiral tube 204 is described herein, those skilled in the art will appreciate that the mold for producing the same will have a mold cavity corresponding to the shape of the spiral tube 204, including the internal flow channel 222 in the form of the thickened longitudinal projection. Those skilled in the art will also appreciate that the mold cavity for the spiral tube 204 will include a series of runners and gates to provide molten material from an exterior of the mold to the mold cavity, such as to one or more of the turns of the spiral fin, as such runners and gates are known in the art.

Figure 4:
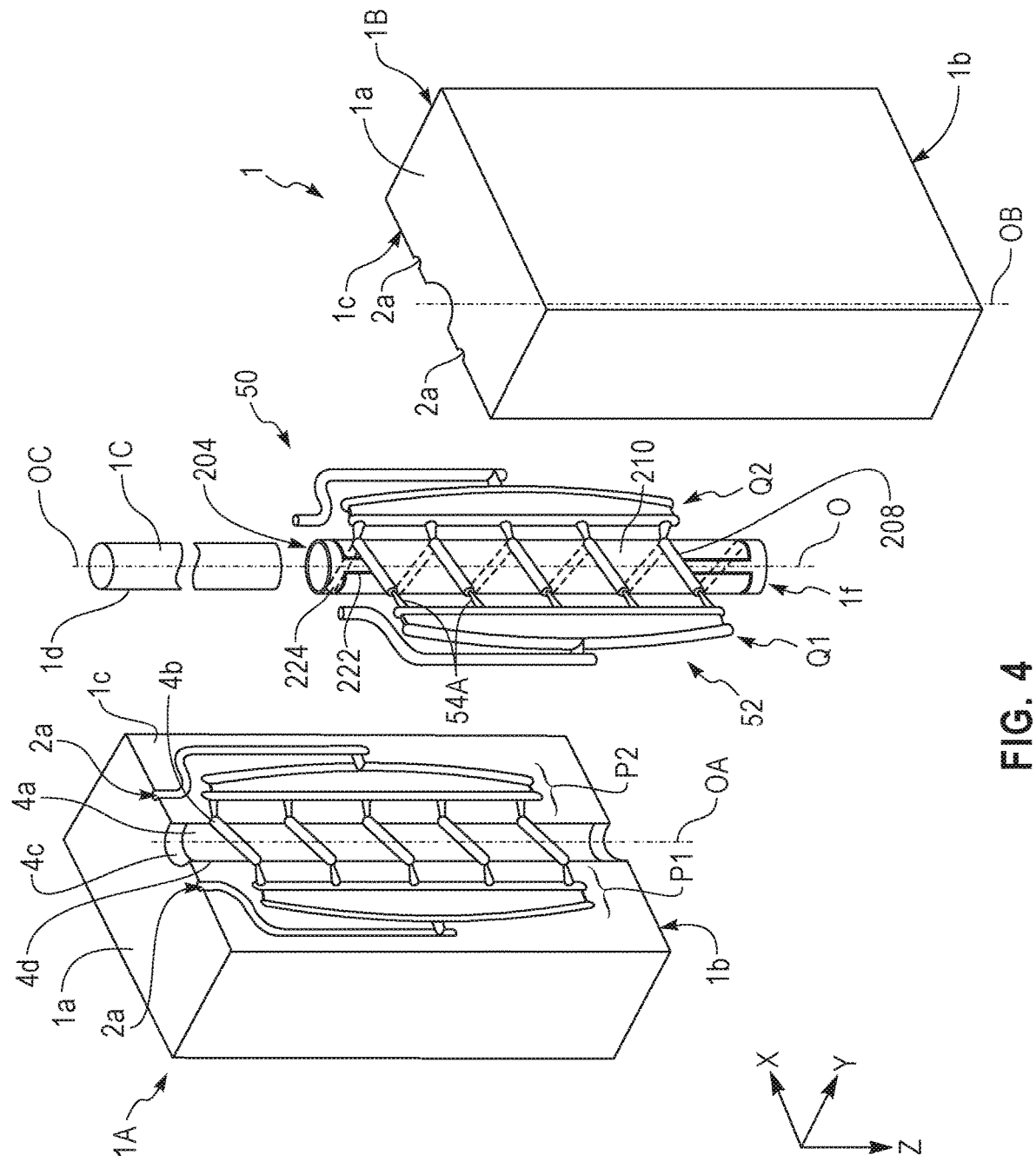
FIG. 4 illustrates a perspective view showing an embodiment of an injection mold for molding the spiral tube of FIG. 1.
Figure 5:
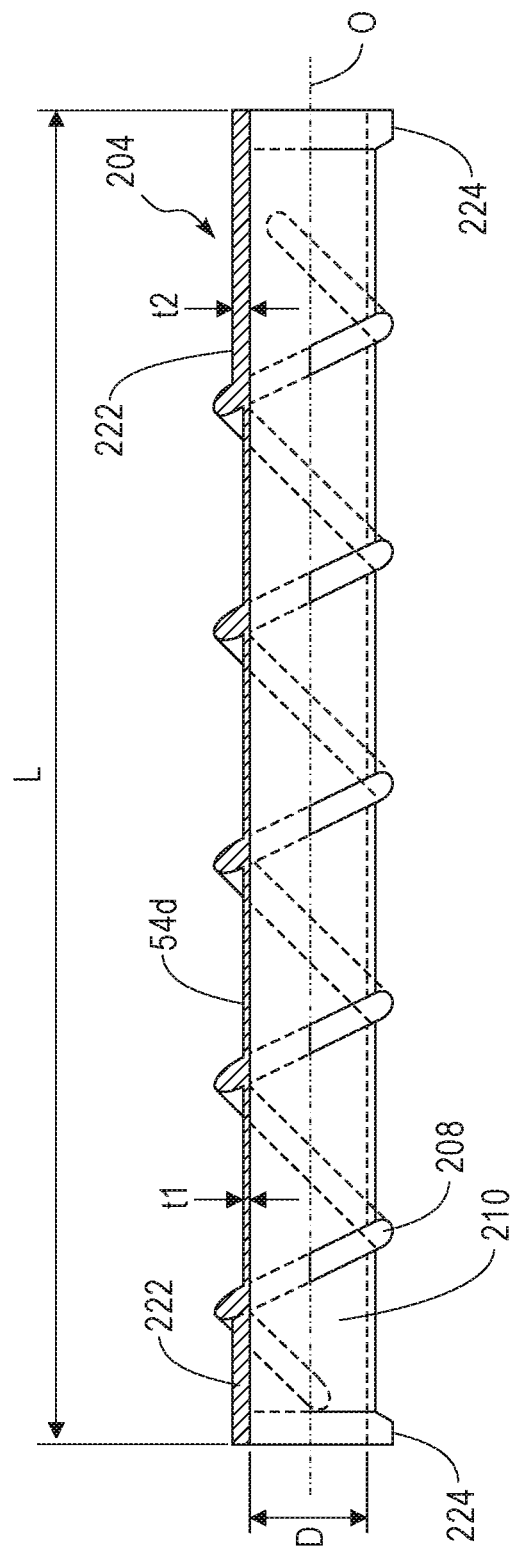
FIG. 5 illustrates a partial cross-sectional view of the molded spiral tube produced by an injection mold according to the mold of FIG. 4.
Figure 6:
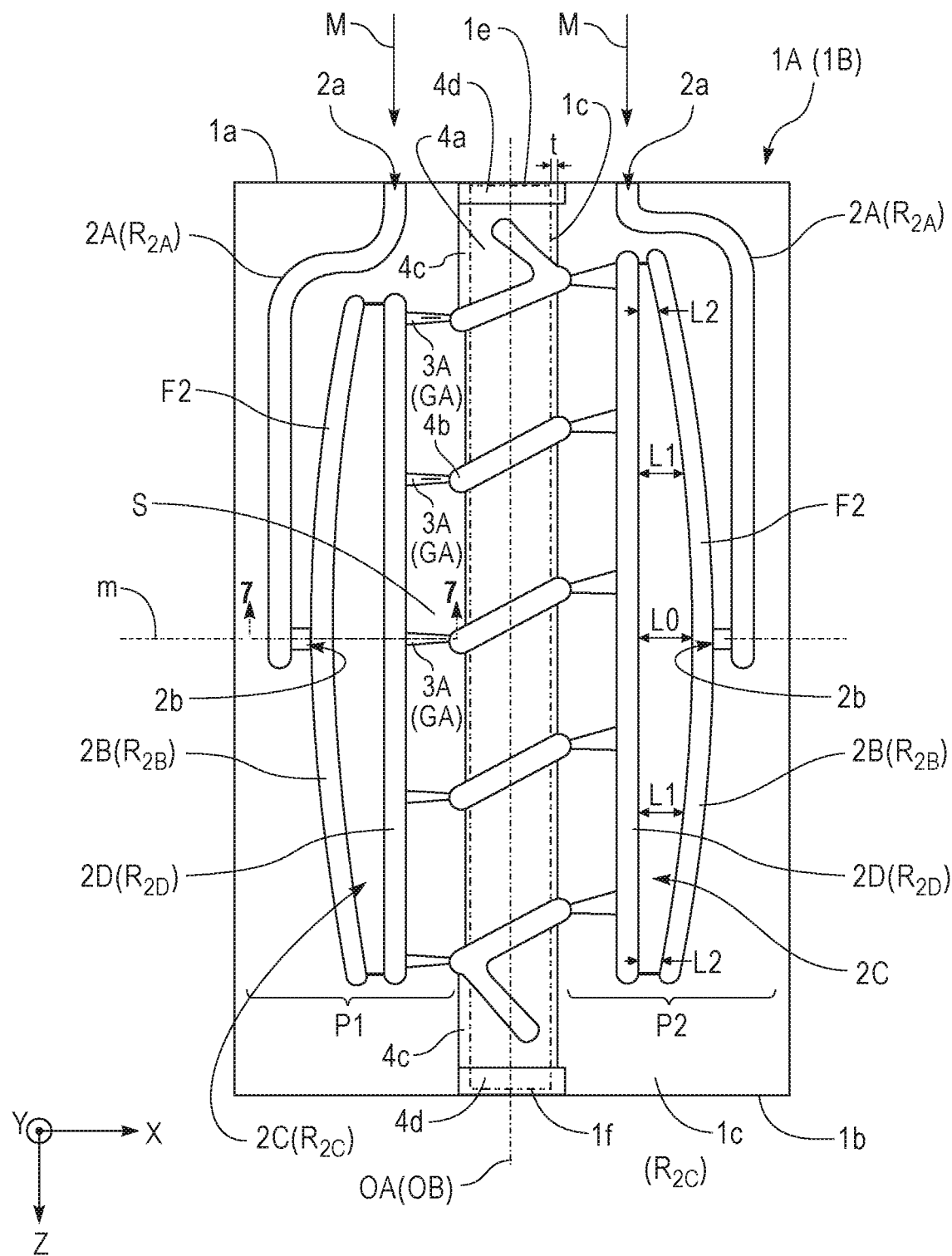
FIG. 6 illustrates a front view of a half of the injection mold of FIG. 4.
Figure 7:
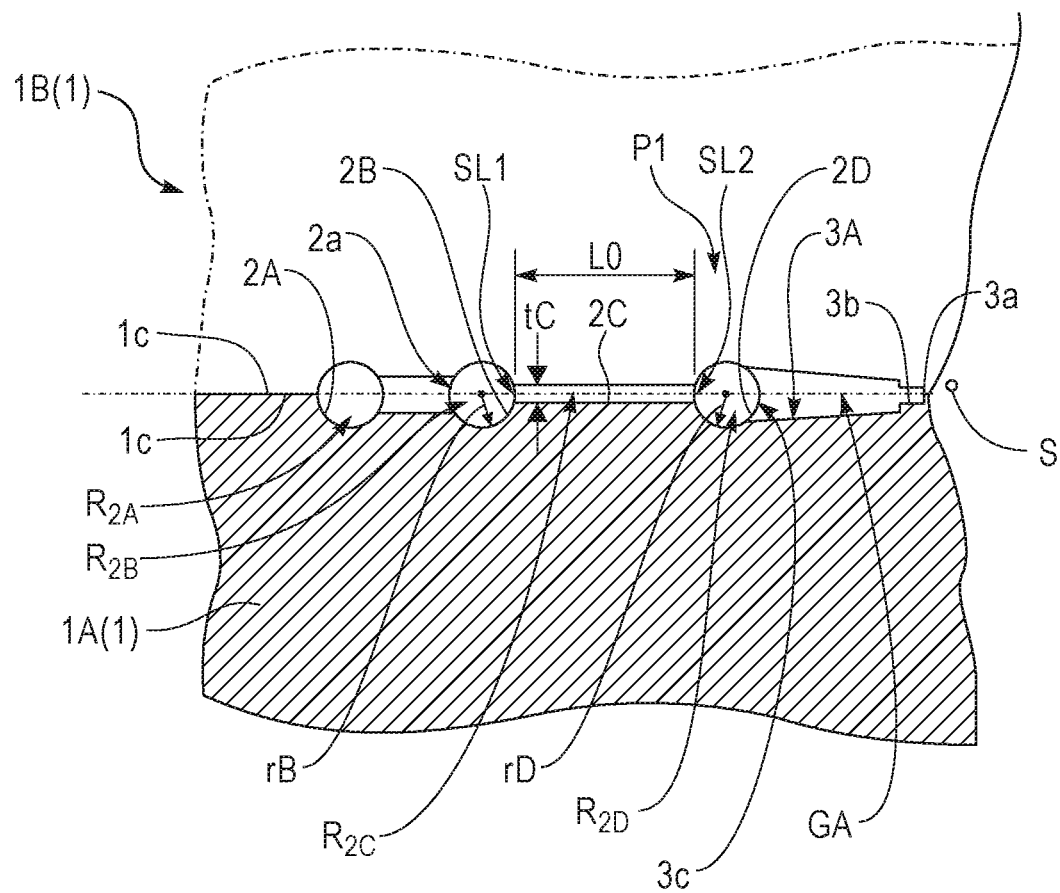
FIG. 7 illustrates a cross-sectional view taken along line 7-7 in FIG. 6.
Figure 8:
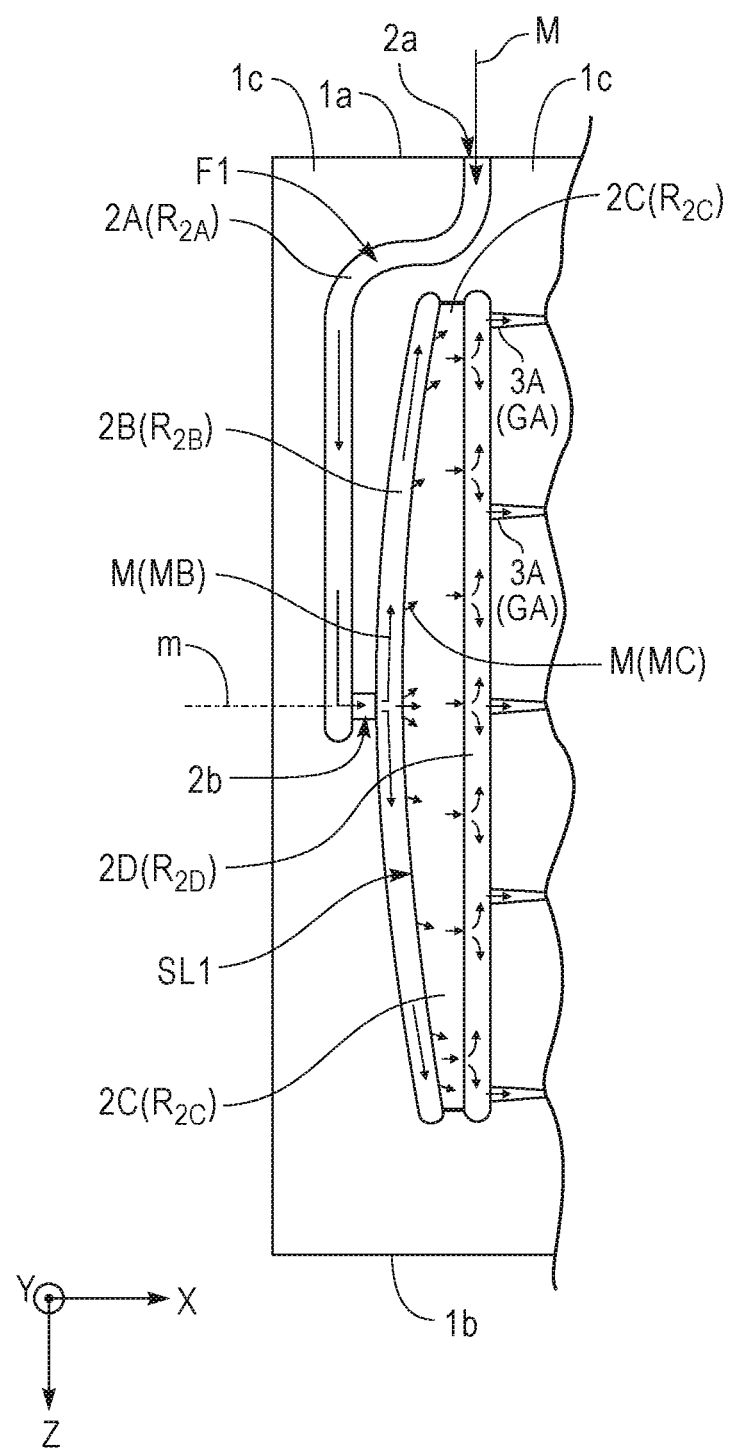
FIG. 8 illustrates a view of injection resin flows in the injection mold of FIG. 4.

An injection mold according to a first embodiment will be described with regard to FIGS. 4-8. FIG. 4 is a schematic perspective view showing an example of an injection mold according to the first embodiment. FIG. 5 is a schematic partial cross-sectional view of the spiral tube 204 molded article produced by the injection mold according to the first embodiment. FIG. 6 is a schematic front view of an injection mold according to the first embodiment. FIG. 7 is a cross-sectional view taken along line 7-7 in FIG. 6. FIG. 8 is a partial view of the mold of FIG. 6 showing resin flow during the molding of the spiral tube 204 molded article. As discussed above, the shape of the molded thin-walled article produced by the injection mold is not particularly limited. The shape of the molded article may be, for example, a box shape, a cylindrical shape, a rod shape, a plate shape, a frame shape, a net shape, or the like, where the corresponding mold cavity would have a corresponding shape.

The mold configuration of the injection mold can be appropriately selected in accordance with the shape of the molded article to be manufactured by the injection mold. For example, the mold configuration of the injection mold may or may not have a slide core.

Hereinafter, an example is described of an injection mold 1 for manufacturing the thin-walled molded article (spiral tube 204) (see FIG. 5) as shown in FIG. 4.

As shown in FIG. 4, the injection mold 1 includes a first slide core 1A, a second slide core 1B, and a core 1C. Although not shown in particular, the injection mold 1 further includes typical members such as a fixed side die plate, a cavity die, and a movable side die plate, for example.

The injection mold 1 is used for manufacturing the spiral tube 204 by injection molding. As discussed above, the spiral tube 204 a tubular portion 210 and a spiral fin 208 protruding from the tubular portion 210. The wall thickness of the tubular portion 210 is constant in the axial direction with the exception of the internal flow channel 222 and end ring 224.

As shown in FIG. 5, the molded spiral tube 204 article has the tubular portion 210 and a spiral fin 208. The tubular portion 210 is a thin-walled tube extending along the central axis O. The tubular portion 210 has an inner diameter D, a wall thickness t1, a wall thickness at the internal flow channel and/or end ring t2 and a length L. For example, L may be 50 mm or more. D may be 5 mm to 50 mm t1 may be 0.1 mm to 2 mm and t2 may be an increased thickness over t1 that provides resin flow to the ends of the thin-walled tube 210 under the conditions discussed above while avoiding a detrimental decrease in flexibility. The spiral fin 208 protrudes in the radial direction from the outer circumferential surface 54d of the tubular portion 210 over the entire circumference of the outer circumferential surface 54d in a spiral or helical manner. The spacing between turns of the spiral fin 208 is not particularly limited.

The spiral tube 204 shown in FIG. 5, also includes the internal flow channel 222 at each end of the thin-walled tube 210 as well as the end ring 224. In the configuration shown in FIG. 5, the internal flow channel 222 extends from the last turn of the spiral fin 208 at each end to the end ring 224.

The material of the spiral tube 204 is not particularly limited as long as it is a resin material capable of being injection molded. The material of the spiral tube 204 may be a hard resin material or a soft resin material such as an elastomer, for example.

Next, the injection molding die 1 for forming the spiral tube 204 will be described.

Hereinafter, descriptions will be given with reference to the XYZ orthogonal coordinate system shown in FIG. 4. The Z-axis is an axis line extending in the moving direction of the movable side die plate or the like. The X-axis is an axis orthogonal to the Z-axis. The Y-axis is an axis orthogonal to the X-axis, in a plane including the X-axis but orthogonal to the Z-axis. The directions along the X axis, Y axis, and Z axis are referred to as the X-direction, the Y-direction, and the Z-direction, respectively.

The first slide core 1A and the second slide core 1B are disposed facing each other in the Y-direction. The first slide core 1A and the second slide core 1B can be slidably moved in at least the Y-direction when the injection molding die 1 is opened and closed. The core 1C is disposed along an axis parallel to the Z-axis. The core 1C is fixed to the movable side die plate, and is movable in the Z-direction together with the movable side die plate. The first slide core 1A and the second slide core 1B form the shape of the outer periphery of the spiral tube 204.

The shapes of the first slide core 1A and the second slide core 1B are similar. Therefore, the description will proceed with a focus on the shape of the first slide core 1A.

The outer shape of the first slide core 1A is a substantially rectangular parallelepiped elongated in the Z-direction. The first slide core 1A has a first end face 1a, parallel to the XY plane, at one end in the Z-direction. When the mold is closed, the first end face 1a faces a fixed side mold plate (not shown) of the injection mold 1.

The first slide core 1A has a second end face 1b, parallel to the XY plane, at the opposite end to the first end face 1a in the Z-direction. When the mold is closed, the second end surface 1b abuts against a movable side die plate (not shown) of the injection mold 1.

The first slide core 1A has a parting face 1c at the surface facing the second slide core 1B. The parting face 1c is a plane parallel to the XZ plane. In each parting face 1c has a recessed portion which forms the outer shape of the spiral tube 204 when the injection mold 1 is closed. A molding space for molding the spiral tube 204 is formed between the recessed portions and the core 1C. The recessed portions (i.e., the molding surfaces), constituting portions of the molding space, form the outer shape of the spiral tube 204 by transferring the surface shape to the injection resin filled in the molding space.

Each parting face 1c has a recessed portion for forming a resin flow path for filling molding resin into the molding space. The recessed portion forming the molding space is composed of a tubular portion molding surface 4a, a spiral fin molding surface 4b, an internal flow channel molding surface 4c and an end ring molding surface 4d. The recessed portion forming the resin flow path is composed of a first resin flow path portion P1 and a second resin flow path portion P2.

The tubular portion molding surface 4a forms the shape of half the outer circumferential surface 54d of the tubular portion 210. The tubular portion molding surface 4a is a semicircular groove extending in the Z-direction with the central axis OA at the center. The semicircular groove is defined as a groove having a semicircular cross-sectional shape orthogonal to the extending direction. In a semicircular groove, the radius of the semicircle in cross section is referred to as the groove radius. The semicircular groove has extending surfaces corresponding to the spiral fin 208, internal flow channels 222 and the end rings 224.

The central axis line OA extends parallel to the Z-axis at the center of the parting face 1c. The groove radius of the tubular portion molding surface 4a is D/2. The tubular portion molding surface 4a passes through between the first end face 1a and the second end face 1b in the Z-direction. The length of the tubular portion molding surface 4a is equal to the total length L of the spiral tube 204.

As shown in FIG. 6, the spiral fin molding surface 4b is a recess in the parting face 1c and the tubular portion molding surface 4a. The spiral fin molding surface 4b forms the spiral fin 208 of the spiral tube 204. The shape of the spiral fin molding surface 4b matches the outer shape of the spiral fin 208. Similarly, the internal flow channel molding surface 4c and end ring molding surface 4d form the internal flow channels 222 and end rings 224 of the spiral tube 204. The internal flow channel molding surface 4c and end ring molding surface 4d are formed at two positions corresponding to each end of the spiral tube 204. The shape of the internal flow channel molding surface 4c and end ring molding surface 4d matches the outer shape of the respective internal flow channel 222 and end ring 224.

As shown in FIG. 4, the core 1C is a cylindrical member having a cylindrical outer circumferential surface 1d. The core 1C forms the shape of the inner circumferential surface Me of the spiral tube 204. The outer diameter of the outer circumferential surface 1d of the core 1C is D, which matches the inner diameter of the spiral tube 204. The length of the core 1C is L, which corresponds to the length of the spiral tube 204. The end faces 1e and if formed at both ends in the axial direction of the core 1C are planes orthogonal to the central axis OC of the outer circumferential surface 1d.

Similar to the first slide core 1A, a tubular portion molding surface 4a and the spiral fin molding surface 4b are also formed in the parting face 1c of the second slide core 1B with a central axis OB as the center. However, the coordinate system in FIG. 6 shows the orientation of the first slide core 1A. The end ring molding surface 4d is also formed in the parting face 1c of the second slide core 1B. Because the internal flow channel 222 may be non-symmetrically arranged on the thin-walled tube 210, the entirety of the internal flow channel molding surface 4c may be formed on only one of the first slide core 1B or the second slide core 1B or a portion of the internal flow channel molding surface 4c may be formed on each of the first slide core 1B and the second slide core 1B.

When the respective parting faces 1c of the first slide core 1A and the second slide core 1B abut when the injection mold 1 is closed, the central axes OA and OB coincide with each other. At this time, the tubular portion molding surfaces 4a, the spiral fin 4b molding surface 4b, the internal flow channel molding surfaces 4c and the end ring molding surfaces 4d facing each other in the Y-direction form the shape of the outer circumferential surface of the spiral tube 204.

As indicated by a two-dot chain line, the core 1C is inserted in the Z direction in the center of the inner space surrounded by the tubular portion molding surfaces 4a. The end faces 1e and if of the core 1C are aligned in the same plane as the first end faces 1a and the second end faces 1b, respectively, of the first slide core 1A and the second slide core 1B.

As a result, a molding space S is formed which is surrounded by the outer circumferential surface 1d of the core 1C, the tubular portion molding surfaces 4a, the spiral fin molding surfaces 4b, the internal flow ring molding surfaces 4c and the end ring molding surfaces 4d.

The first resin flow path portion P1 and the second resin flow path portion P2 have a symmetric shape with respect to a plane of symmetry passing through the central axis line OA and parallel to the YZ plane. Hereinafter, the description will proceed with a focus on the shape of the first resin flow path portion P1.

The first resin flow path portion P1 includes an inlet runner groove 2A, a first runner groove 2B, a second runner groove 2C, a third runner groove 2D, and gate grooves 3A. The inlet runner groove 2A is a semicircular groove extending between the injection port 2a and the opening 2b. The groove radius of the inlet runner groove 2A is constant. The injection port 2a is a semicircular opening provided for the purpose of injecting the injection resin M into the inlet runner groove 2A. The injection port 2a is open to the first end face 1a.

The opening 2b is formed at a position facing, in the X-direction, a central portion of the spiral fin molding surface 4b (i.e., the Z-direction). The path of the inlet runner groove 2A is not particularly limited. In FIG. 6, the inlet runner groove 2A extends in the Z-direction from the injection port 2a, bends in the X-direction away from the central axis OA, bends in the Z-direction toward the reference plane m, and, at a position facing the opening 2b, forms a path that bends in the X-direction toward the opening 2b. The inner diameter of the inlet runner groove 2A is set to an appropriate size that allows the molten injection resin M to flow well.

The first runner groove 2B is a semicircular groove along a path concavely curved toward the central axis OA. Both ends of the first runner groove 2B extend in the X-direction to positions facing the gate grooves 3A, which will be described later, on both sides of the reference plane m and farthest from the reference plane m. The first runner groove 2B is symmetric with respect to the reference plane m. The curved shape of the first runner groove 2B is set for the purpose of changing the X-direction length of a second runner groove 2C, described later, as a function of the position in the Z-direction.

As shown in FIG. 7, the groove radius of the first runner groove 2B is a constant value rB. As shown in FIG. 7, the second runner groove 2C is a recess communicating with a side of the first runner groove 2B facing the third runner groove 2D, which will be described later. The depth of the second runner groove 2C from the parting face 1c is tC, where tC<rB.

As shown in FIG. 6, the second runner groove 2C communicates with the first runner groove 2B over substantially the entire length of the first runner groove 2B. The width of the second runner groove 2C in the X-direction changes in the Z-direction according to the amount of curvature of the first runner groove 2B. Further, the shape of the second runner groove 2C, as viewed in the Y-direction, is symmetric with respect to the reference plane m.

The third runner groove 2D is a semicircular groove linearly extended in the X-direction. The third runner groove 2D is at a position facing the entire first runner groove 2B in the X-direction with the second runner groove 2C interposed therebetween. The second runner groove 2C communicates with the third runner groove 2D. The length of the third runner groove 2D has the same length as a molding range of the first runner groove 2B in the Z-direction. The center of the third runner groove 2D in the Z-direction is located on the reference plane m. As shown in FIG. 7, the groove radius of the third runner groove 2D is a constant value rD, where rD>tC.

The gate groove 3A is a recessed portion for enabling communication between different portions of the spiral fin molding surface 4b and the third runner groove 2D facing the spiral fin molding surface 4b in the X-direction. The gate groove 3A is a semicircular groove having an axis extending in the X-direction as the center. For example, the gate groove 3A has a shape obtained by dividing the shape of a pin gate by half from the center. As shown in FIG. 7, a gate opening 3a that opens to the molding space S optimizes the speed of the injection resin M that enters the molding space S are formed at the distal end of the gate groove 3A. In the gate groove 3A, the radius of the opening 3c communicating with the third runner groove 2D is less than rD. The gate grooves 3A divide the injection resin M flowing in the third runner groove 2D in the Z-direction toward the spiral fin molding surface 4b.

As shown in FIG. 6, a first resin flow path portion P1 and a second resin flow path portion P2 similar to those in the first slide core 1A are also formed on the parting face 1c of the second slide core 1B. When the respective parting faces 1c of the first slide core 1A and the second slide core 1B come in contact with each other when the injection molding die 1 is closed, the respective first resin flow path portions P1 and the respective second resin flow path portions P2 facing each other in the Y-direction form resin flow paths F1 and F2 having circular and rectangular flow path cross-sections.

The resin flow paths F1 and F2 each include an inlet runner $R_{2A}$ (i.e., an upstream runner), a first runner $R_{2B}$ (i.e., a downstream runner, first circular tube flow path, first runner portion), a second runner $R_{2C}$ (i.e., a downstream runner, second runner portion, plate-shaped flow path), a third runner $R_{2D}$ (i.e., a downstream runner, second circular tube flow path, third runner portion), and gates GA.

The inlet runner $R_{2A}$ is a flow path formed by combining the inlet runner grooves 2A facing each other in the Y-direction. The inlet runner $R_{2A}$ constitutes an upstream runner having an injection port 2a into which the injection resin M is injected. The first runner $R_{2B}$, the second runner $R_{2C}$, and the third runner $R_{2D}$ communicate with the inlet runner $R_{2A}$ and the gates GA and constitute a downstream runner that distributes the injection resin M injected into the injection port 2a to the gates GA.

The first runner $R_{2B}$ is a flow path formed by combining the first runner grooves $2_B$ facing each other in the Y-direction. The first runner $R_{2B}$ is a first circular tube flow path having a first inner diameter of 2×rB. Openings 2b are opened at the center of the first runners $R_{2B}$ (i.e., a center portion). The first runner $R_{2B}$ faces the respective gates GA, with the second runner $R_{2C}$ and the third runner $R_{2D}$ interposed therebetween, and extends along with the positions of the gates GA.

The second runner $R_{2C}$ is a flow path formed by combining the second runner $R_{2C}$ facing each other in the Y-direction. The second runner $R_{2C}$ is a plate-shaped flow path having a flow path width of 2×tC in the thickness direction. The second runner $R_{2C}$ forms a slit SL1 having a width of 2×tC (see FIG. 7), which is the same as the flow path width over the approximate overall extending direction of the first runner $R_{2B}$ on the X-direction side of the first runner $R_{2B}$. Since the flow path width is smaller than the first inner diameter, the flow path cross-section of the second runner $R_{2C}$ has a higher resistance than the flow path cross-section of the first runner $R_{2B}$.

As shown in FIG. 6, the length of the second runner $R_{2C}$ in the direction toward the gates GA (i.e., the X-direction) decreases as the distance from the reference plane m in the extending direction of the first runner $R_{2B}$ increases; for example, the length of the second runner $R_{2C}$ at the gate GA at the center in the Z-direction (referred to as the first gate) is L0. The length of the second runner $R_{2C}$ at the point corresponding to the gate GA, disposed next to the central gate GA, is L1, where L1<L0. The length of the second runner $R_{2C}$ at each gate GA disposed farther from the reference plane m than each gate GA is L2, where L2<L1. The lengths L0, L1, and L2 are set so that the arrival times of the injection resin M from the opening 2b to the first gate, the gates GA, and the second gates are the same. Each length can be determined, for example, by flow simulation of the injection resin M.

The third runner $R_{2D}$ is a flow path formed by combining the third runner $R_{2D}$ facing each other in the Y-direction. The third runner $R_{2D}$ is a second circular tube flow path having a second inner diameter of 2×rD. Since the second inner diameter is larger than the flow path width of the second runner $R_{2C}$, the flow path cross section of the third runner $R_{2D}$ has a lower resistance than the flow path cross section of the second runner $R_{2C}$. The second runner $R_{2C}$ forms a slit SL2 having a width of 2×tC (see FIG. 7), which is the same as the flow path width over the approximate overall extending direction of the third runner $R_{2D}$ on the X-direction side of the third runner $R_{2D}$. The gate GA is a flow path formed by combining the gate grooves 3A facing each other in the Y-direction.

With such a configuration, in the second runner $R_{2C}$, the shortest distance of the flow path from the first runner $R_{2B}$ to each of the gates GA differs depending on the shortest distance between the opening 2b and each of the gates GA. For example, in the second runner $R_{2C}$, the shortest distance in the flow path from the first runner $R_{2B}$ to the first gate closest to the opening 2b is L0. On the other hand, in the flow path of the first runner $R_{2B}$ in which the shortest distance from the opening 2b sequentially becomes longer, the flow path of the second runner $R_{2C}$ at the point corresponding to the second gate, the shortest distance from the first runner $R_{2B}$ toward the gate is shorter as the shortest distance from the opening 2b to each gate becomes longer, as in L1 and L2.

A manufacturing process of the spiral tube 204 using the injection mold 1 will now be described with reference to FIG. 8. FIG. 8 is a view of injection resin flows in the injection mold according to the first embodiment.

When manufacturing the spiral tube 204, the injection mold 1 is attached to an injection molding machine (not shown). While the injection mold 1 is closed, the molding space S and the resin flow paths F1, F2, which communicate with the molding space S through the spiral fin molding surface 4c, are formed inside the assembly consisting of the first slide core 1A, the second slide core 1B, and the core 1C. Each of the injection ports 2a, in the first end face 1a, for the resin flow paths F1, F2 communicates with a sprue (not shown) in a cavity mold plate (not shown).

The injection resin M injected from an injection molding machine in a molten state is injected into the resin flow paths F1, F2 through the sprue and each of the injection ports 2a. The injection amount of the injection resin M is determined in advance according to the sum total volume of the molding space S and the resin flow paths F1 and F2. Since the resin flow paths F1 and F2 are similar flow paths except for being in different positions, an example of only the resin flow path F1 will be described below.

As shown in FIG. 8, the injection resin M injected into the injection port 2a for the resin flow path F1 flows along the path in the inlet runner $R_{2A}$ toward the opening 2b. In the vicinity of the opening 2b, the injection resin M flows in the X-direction in which the distal ends of the inlet runner $R_{2A}$ extend. When the injection resin M enters the first runner $R_{2B}$ from the opening 2b, the injection resin M flows toward both ends of the first runner $R_{2B}$. Since the first runner $R_{2B}$ extends in the Z-direction in the vicinity of the opening 2b, a T-shaped branch flow path branching in two directions, from the X-direction to the Z-direction, is formed in the vicinity of the opening 2b. Therefore, the flow of the injection resin M is bisected into a first runner $R_{2B}$ toward the first end face 1a and a first runner $R_{2B}$ toward the second end face 1b. Since the slit SL1 is opened on the side of the first runner $R_{2B}$, a part of the resin MC of the injection resin M flows into the second runner $R_{2C}$ through the slit SL1.

However, since the opening width (i.e., the width in the Y-direction) of the slit SL1 is smaller than the first inner diameter of the first runner $R_{2B}$, the flow path resistance of the second runner $R_{2C}$ is larger than the flow path resistance of the first runner $R_{2B}$. As a result, resin MB, which is the injection resin M excluding the resin MC, flows in the extending directions of the first runners $R_{2B}$. The amount of the resin MB is markedly larger than that of the resin MC.

The flow velocity of the resin MC is proportionally lower than the flow velocity of the resin MB in accordance with the cross-sectional size of the flow path in the flow direction. Therefore, the resin MC fills the first runner $R_{2B}$ prior to the resin MC passing through the third runner $R_{2D}$ and flowing into the gates GA. At the time at which the filling of injection resin M in the first runner $R_{2B}$ is completed (hereinafter referred to as the first filling completion time), an approximately uniform injection pressure is applied to all of injection resin M in the first runner $R_{2B}$ so that the injection resin M is extruded entirely into the second runner $R_{2C}$ from the slit SL1.

Until the first filling completion time, the resin MC gradually flows into the second runner $R_{2C}$. Since it takes a time corresponding to the length of the first runner $R_{2B}$ to fill the first runner $R_{2B}$ with the resin MB, the timing of the resin MC flowing into the second runner $R_{2C}$ is delayed the farther the position from the reference plane m in the Z-direction. Pressure applied to the resin MC is lower as the distance from the reference plane m in the Z-direction increases. As a result, the amount of the resin MC flowing into the second runner $R_{2C}$ decreases as the resin MC moves away from the reference plane m in the Z-direction. Similarly, the flow velocity of the resin MC decreases as the resin MC moves away from the reference plane m in the Z-direction.

Therefore, when the first runner $R_{2B}$ is linear, the resin MC traveling in the second runner $R_{2C}$ spreads in a fan-shape in which the flow length of the resin MC at the reference plane m is the longest. However, since the first runner $R_{2B}$ is concavely curved toward the third runner $R_{2D}$, the front edge of the resin MC becomes flat in accordance with the amount of curvature of the first runner $R_{2B}$. Therefore, by appropriately setting the magnitude of the resistivity of the flow path cross-section of the second runner $R_{2C}$ and the curvature of the first runner $R_{2B}$, the difference in the filling times of the second runner $R_{2C}$ in the Z-direction is reduced.

When the outlet of the second runner $R_{2C}$ is linear along the third runner $R_{2D}$, the curvature of the first runner $R_{2B}$ defines the distribution of flow path lengths in the second runner $R_{2C}$ in the extending direction of the first runner $R_{2B}$. In this manner, the front edge of the resin MC becomes flat in the X-direction as the resin MC advances toward the third runner $R_{2D}$. As a result, each position along the Z-direction of the second runner $R_{2C}$ is filled at substantially the same time. The time at which the filling of the second runner $R_{2C}$ is completed is hereinafter referred to as the second filling completion time.

The resin MC flowing into the second runner $R_{2C}$ is turbulent before the first filling completion time. If, in an effort to further downsize the injection mold 1, the length in the X-direction in the second runner $R_{2C}$ is shortened, the front edge position in the X-direction of the resin MC may vary to some extent as a function of the position in the Z-direction. By providing the third runner $R_{2D}$ in the downstream runner, deviations in arrival times of the injection resin M to each of the gates GA due to the disturbance of the front edge of the resin MC are reduced.

The resin MC crossing the second runner $R_{2C}$ in the X-direction flows into the third runner $R_{2D}$ through the slit SL2. The second inner diameter of the third runner $R_{2D}$ is larger than the opening width (i.e., the width in the Y-direction) of the slit SL2. When the resin MD entering the third runner $R_{2D}$ effuses into the third runner $R_{2D}$, the resin MD is dispersed and the flow velocity of the resin MD decreases. Due to this, after the resin MD fills the third runner $R_{2D}$ to some extent, the resin MD flows into the molding space S from the nearby gates. The resin flowing into the internal flow channel molding spaces 4c allows the resin to flow towards the ends of the tubular portion molding surface 4a to completely fill the molding space S corresponding to the ends of the tubular portion molding surfaces 4a and to further fill the end ring molding surfaces 4d, if provided.

As a result, no voids are formed at the ends of the resulting spiral tube 204 and even if the amounts of the resin MD in the longitudinal direction of the third runner $R_{2D}$ vary due to variations of the front edge of the resin MC, the times at which the resin MD arrive at the respective gates are equalized. As described above, in the present embodiment, even if the positions in the Z-direction of the gates GA are different from each other, the injection resin M reaches each of the gates GA at the same time.

After the injection resin M fills the third runner $R_{2D}$, the injection resin M fills the molding space S through the gates GA since a substantially uniform injection pressure is applied to all of the injection resin M in the downstream runner. The injection resin M filled into the molding space S is cooled by conduction of heat to the first slide core 1A, the second slide core 1B, and the core 1C. As shown in FIG. 4, when the injection resin M is left for a period of time at which the temperature of the injection resin M becomes equal to or lower than the glass transition point, a molded body 50 in which the injection resin M in the injection mold 1 is solidified is formed. Thereafter, the injection mold 1 is opened. When the injection mold 1 is opened, the first slide core 1A and the second slide core 1B are separated from each other in the Y-direction. This enables demolding of the molded body 50. The molded body 50 includes the spiral tube 204 and flow path resin portions Q1, Q2.

The flow path resin portion Q1 is formed by solidifying the injection resin M filled in the resin flow path F1. The flow path resin portion Q1 includes a runner resin portion 52 and gate resin portions 53A. The runner resin portion 52 is a portion to which the shapes of the upstream runner and the downstream runner are transferred. The gate resin portions 53A are portions to which the shapes of the gates GA are transferred, respectively. The flow path resin portion Q2 is formed by solidifying the injection resin M filled in the resin channel F2. Like the flow path resin portion Q1, the flow path resin portion Q2 includes a runner resin portion 52 and gate resin portions 53A. The molded article 54 is manufactured by separating the flow path resin portions Q1, Q2 from the molded body 50 by secondary operations known in the art.

Figure 9:
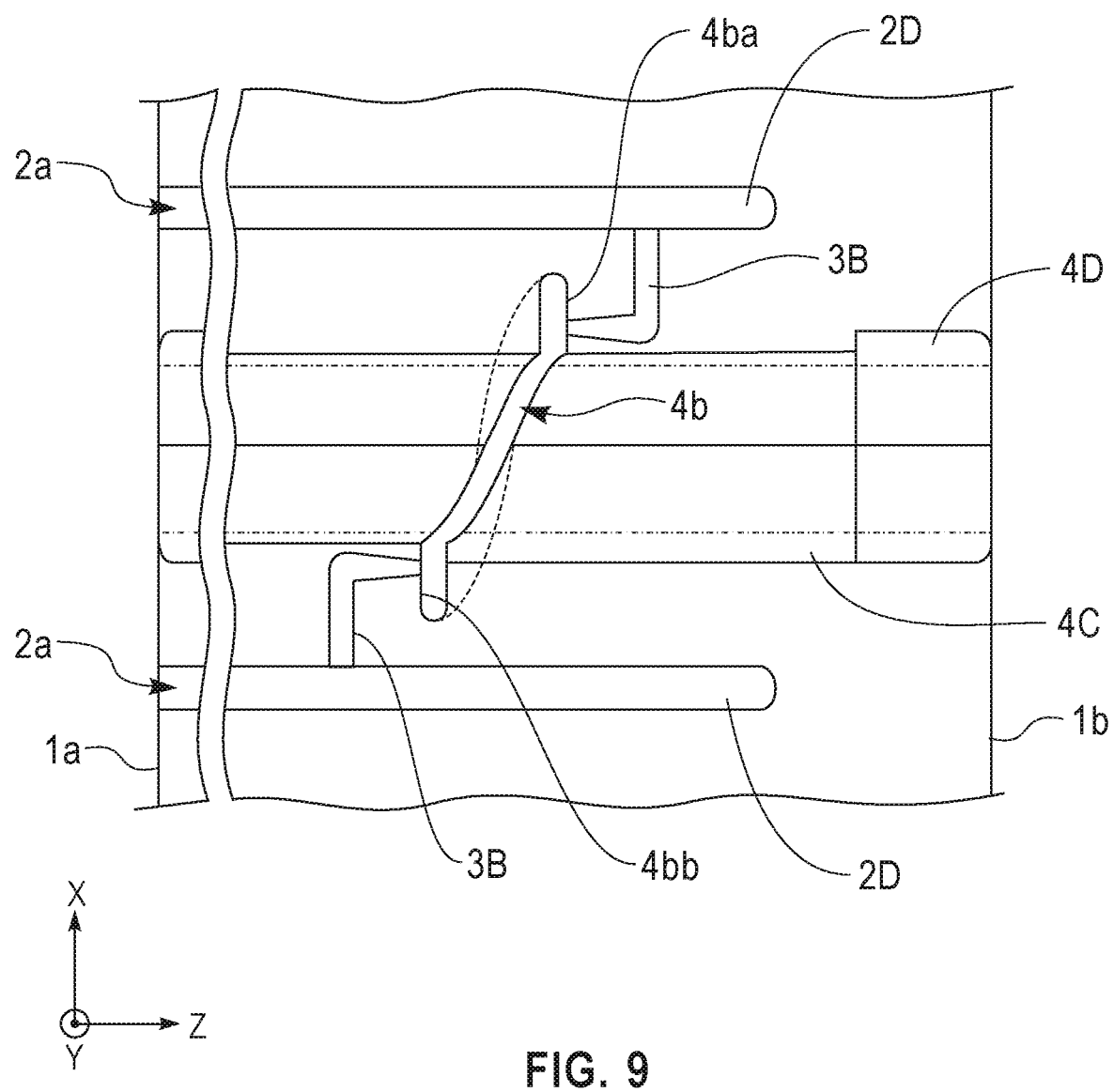
FIG. 9 illustrates an alternative gating configuration for the mold of FIG. 6.

Referring now to FIG. 9, there is shown an alternative gating configuration from the gating configuration shown in FIG. 6 in which like features are referenced with like reference characters from FIG. 6. In FIG. 9, the gates 3B providing resin from runner grooves 2D can alternatively have an output 3a on side surfaces 4ba, 4bb of each turn of the spiral fin molding surface 4b. In such configuration, the internal flow channel molding surface 4c can extend from a side surface 4ba of the spiral fin molding surface 4b opposite to the side surface 4bb where the gate 3B enters the spiral fin molding surface 4b. As discussed above, such internal flow channel molding surface 4c can extend to a corresponding end of the thin-walled tube molding surface 4a or alternatively, to the end ring molding surface 4d, if provided. Although only one turn of the spiral fin molding surface 4b is shown in FIG. 9, all of such turns can have a similar gate configuration or some of such turns, such as only the end turns, may have the gate configuration of FIG. 9.

The internal flow channel 222 described above can be configured to provide a necessary resin flow to the end of a thin-walled tube molded product while maintaining a desired requirement of flexibility, which has particular utility for use in spiral tubes used on an insertion section of an endoscope. Rather than thickening the wall of the entire tube 210 or thickening large portions thereof, the internal flow channel 222 enables a highly controllable and directable plastic flow towards the last area of fill, without detrimentally increasing the bending stiffness of the tube 210. The spiral tube 204, in order to be used in endoscopic procedures, must maintain a desired amount of flexibility.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be construed to cover all modifications that may fall within the scope of the appended claims.

What is claimed is:

1. A polymeric device comprising:
    an elongated hollow tube having an outer surface, the elongated hollow tube being configured to be rotatably attached to an insertion section of an endoscope; and
    a spiral fin wound around the outer surface of the hollow tube;
    wherein the hollow tube and the spiral fin are formed of a single unitary piece through a molding process.

2. The polymeric device of claim 1, further comprising a longitudinal projection projecting from the outer surface of the hollow tube, the longitudinal projection having a greater thickness than other portions of the hollow tube and the longitudinal projection extending at least a portion of a longitudinal length of the hollow tube.

3. The polymeric device of claim 2, wherein the longitudinal length of the longitudinal projection extends from a portion of the spiral fin nearest an end of the hollow tube to the end of the hollow tube.

4. The polymeric device of claim 2, further comprising an end ring formed at an end of the hollow tube, the end ring having a thickness projecting from the outer surface of the hollow tube, the longitudinal length of the longitudinal projection extends from a portion of the spiral fin nearest the end of the hollow tube to the end ring.

5. The polymeric device of claim 2, wherein the longitudinal projection extends at least the portion of the longitudinal length of the hollow tube at a single circumferential position.

6. A polymeric tubular member comprising:
    an elongated hollow tube having an outer surface;
    a spiral fin wound around the outer surface of the hollow tube; and
    a longitudinal projection projecting from the outer surface of the hollow tube, the longitudinal projection having a greater thickness than other portions of the hollow tube and the longitudinal projection extending at least a portion of a longitudinal length of the hollow tube;
    wherein the hollow tube, the spiral fin and the longitudinal projection are formed of a single unitary piece through a molding process.

7. The polymeric tubular member of claim 6, wherein the longitudinal length of the longitudinal projection extends from a portion of the spiral fin nearest an end of the hollow tube to the end of the hollow tube.

8. The polymeric tubular member of claim 6, further comprising an end ring formed at an end of the hollow tube, the end ring having a thickness projecting from the outer surface of the hollow tube, the longitudinal length of the longitudinal projection extends from a portion of the spiral fin nearest the end of the hollow tube to the end ring.

9. The polymeric tubular member of claim 6, wherein the longitudinal projection extends at least the portion of the longitudinal length of the hollow tube at a single circumferential position.

10. The polymeric device of claim 1, wherein the elongated hollow tube having a wall thickness between 0.1 and 2 mm.

11. The polymeric device of claim 1, wherein the elongated hollow tube having a longitudinal length of 50 mm or more.

12. The polymeric tubular member of claim 6, wherein the elongated hollow tube having a wall thickness between 0.1 and 2 mm.

13. The polymeric tubular member of claim 6, wherein the elongated hollow tube having a longitudinal length of 50 mm or more.

* * * * *